(12) United States Patent
Derrieu

(10) Patent No.: US 8,501,799 B2
(45) Date of Patent: Aug. 6, 2013

(54) PHARMACEUTICAL COMPOSITION CONTAINING AN N-PHENYLPYRAZOLE DERIVATIVE, AND USE THEREOF FOR PREPARING A TOPICAL VETERINARY FOR FLEA CONTROL

(75) Inventor: Guy Derrieu, Cagnes sur Mer (FR)

(73) Assignee: Virbac, Carros (FR)

( * ) Notice: Subject to any disclaimer, the term of this patent is extended or adjusted under 35 U.S.C. 154(b) by 0 days.

(21) Appl. No.: 13/132,996

(22) PCT Filed: Dec. 16, 2008

(86) PCT No.: PCT/FR2008/001756
§ 371 (c)(1),
(2), (4) Date: Aug. 17, 2011

(87) PCT Pub. No.: WO2010/070210
PCT Pub. Date: Jun. 24, 2010

(65) Prior Publication Data
US 2012/0029043 A1  Feb. 2, 2012

(51) Int. Cl.
| | |
|---|---|
| *A01N 47/02* | (2006.01) |
| *A01N 25/02* | (2006.01) |
| *A01P 7/04* | (2006.01) |
| *A61K 31/415* | (2006.01) |
| *A61K 47/34* | (2006.01) |
| *A61K 9/00* | (2006.01) |
| *A61P 33/14* | (2006.01) |

(52) U.S. Cl.
USPC .................. 514/407; 548/356.1; 424/405

(58) Field of Classification Search
None
See application file for complete search history.

(56) References Cited

U.S. PATENT DOCUMENTS 6,395,765 B1 * 5/2002 Etchegaray ................ 514/407
6,797,724 B2 * 9/2004 Etchegaray et al. ........ 514/407

FOREIGN PATENT DOCUMENTS

WO    WO 97/12521    4/1997

OTHER PUBLICATIONS

Definition of Prevent, Princeton University "About WordNet." WordNet. Princeton University. 2010. <http://wordnet.princeton.edu> accessed Sep. 7, 2012.*
International Search Report and Written Opinion for International Applicaton No. PCT/FR2008/001756, mailed Sep. 30, 2009.
Merial Animal Health Limited; "Summary of product and characteristics. Frontline Spot on Cat"; Internet Article; [online]; [Retrieved on Aug. 26, 2008]; Retrieved from the Internet <URL: http://www.vmd.gov.uk/espcsite/Documents/138128.doc; XP007905533; 7 pages.

* cited by examiner

*Primary Examiner* — Sreeni Padmanabhan
*Assistant Examiner* — Irina Neagu
(74) *Attorney, Agent, or Firm* — Alston & Bird LLP

(57) ABSTRACT

The invention relates to a liquid pharmaceutical composition that contains N-phenylpyrazole derivative as an active principle, benzyl alcohol, and an appropriately selected organic solvent, and to the use of such a composition for preparing a topically applied antiparasitic veterinary drug for preventing and/or treating flea infestation in pets, in particular, in dogs and cats.

15 Claims, No Drawings

PHARMACEUTICAL COMPOSITION CONTAINING AN N-PHENYLPYRAZOLE DERIVATIVE, AND USE THEREOF FOR PREPARING A TOPICAL VETERINARY FOR FLEA CONTROL

FIELD OF THE INVENTION

The present invention relates to a liquid pharmaceutical composition containing, as active principle, an N-phenylpyrazole derivative, benzyl alcohol and a suitably selected organic solvent, and also to the use of such a composition for the preparation of an antiparasitic veterinary medicament for topical use for preventing and/or treating flea infestations on pets, in particular cats and dogs.

BACKGROUND OF THE INVENTION

Pets are often infested with one or more parasites that feed on blood, such as cat or dog fleas, ticks, or mange.

Fleas are wingless insects, with a laterally compressed body and highly developed legs, adapted for jumping. They are ectoparasites, which suck the blood of mammals or birds. The approximately 2000 listed species belong to the order of Siphonaptera. Two species of flea are commonly encountered in Europe; they are the cat flea (*Ctenocephalides felis*) and the dog flea (*Ctenocephalides canis*) which live in the animals' fur. The cat flea, which is the most common, is capable of reproducing both on cats and dogs. It can also attack man and other pets, but cats are the main host responsible for infestation when cats and dogs live in the same environment.

Fleas have a complex life cycle with four distinct stages: egg, larva, nymph and adult. They mate within the first 8 to 48 hours following acquisition by the host, after their first blood meal. The females thus begin to lay 24 to 48 hours after this first blood meal. The adult flea generally lays on the animal. The eggs laid on the animal do not remain thereon, but fall to the floor. Under optimum conditions, the female may lay more than 25 eggs per day. She will lay several hundred in her lifetime. After a few days, a white, hairy, worm-like larva about 1.5 mm long is born. The larva feeds on organic debris, larval remains and dry blood excreted by the adults. The larval state lasts for 1 to 3 weeks, if the conditions are favorable (18° to 27° C. and 70% relative humidity). The larva then spins a cocoon and transforms into a nymph. Normally, the nymph develops in 1 to 2 weeks, but passage to the adult state may take up to 1 year, if the conditions are unfavorable. The adult flea (small and black) emerges from the cocoon when it detects vibrations, heat and a higher concentration of carbon dioxide, which takes place during the passage of a cat, a dog . . . or a human! It then jumps onto the victim, feeds immediately on its blood and rapidly becomes engorged, taking a lighter reddish-brown color. The adult flea lives for 6 to 12 months. Without food, it can survive for up to 2 months.

Flea bites cause itching, in animals and in man. Flea saliva (secreted at each bite) may also, depending on the individual, lead to immediate or delayed allergic reactions. These reactions are reflected by various skin lesions and itching. Two types of flea-related dermatosis are distinguished, namely pulicosis and flea-bite allergic dermatitis. Whereas, in both cases, the dermatosis results from a more or less pronounced infestation with fleas, it is only in the second case that an allergic phenomenon is associated. Flea-bite allergic dermatitis (FBAD) is the most frequent cause of pruritus in dogs. In France, in adult dogs, it thus represents close to half the pruriginous dermatoses. Close to 80% of dogs presenting FBAD also have atopic dermatitis. Reciprocally, two out of three atopic dogs have FBAD. It is thus likely that atopic dogs are predisposed to developing a flea-bite allergy and that infestation with fleas is a triggering factor for atopic dermatitis. This justifies the need for very rigorous antiflea control in the case of atopic dogs or dogs belonging to at-risk breeds. Furthermore, FBAD is probably the main cause of reappearance of pruritus in the case of desensitized atopic dogs.

Fleas of the genus *Ctenocephalides* are moreover intermediate hosts of *Dipylidium caninum*, which is a parasitic worm of the small intestine of cats and dogs. The carnivore becomes infested by swallowing the parasitized fleas. This infestation may lead to anal pruritus, engorgement of the anal sacs, and also to dermatitis of the perineal region. This is why it is occasionally recommended to regularly worm animals in addition to combating fleas.

Similarly, ticks (*Rhipicephalus* sp., *Ixodes* sp., *Dermacentor* sp., *Amblyomma* sp., etc.) may also cause the animal stress and be harmful to its health. They may also be harmful to man. However, the most serious problem concerning ticks is that they are a vector of pathogens that affect animals as much as man. Among the major diseases that need to be avoided, mention may be made of Borellioses (Lyme's disease caused by *Borellia burgdorferi*), Babesioses (piroplasmoses caused by *Babesia* sp.) and Rickettsioses. Ticks may also release toxins with paralyzing and inflammatory, and occasionally fatal, properties.

Mange (*Demodex* sp., *Sarcoptes* sp., *Otodectes* sp., etc.) is particularly difficult to combat since there are very few efficient active materials. It requires frequent treatments.

Infestation with these various parasites, and most particularly with fleas, thus represents a major health problem for the infested animals and imposes the need for suitable treatments. The treatment should in particular not only have immediate efficacy (fast-acting) but also prolonged efficacy over time (remanence) so as to avoid, on the one hand, repeated treatments, and, on the other hand, any risk of infestation and/or reinfestation for a prolonged period. The flea, in particular, must be eliminated before it reproduces and begins to lay.

Many insecticidal substances that are more or less active and more or less expensive exist. Resistance phenomena appear associated with their use, and this is especially the case during the use of carbamates, organophosphorus compounds and pyrethroids.

Moreover, patent applications EP 0 295 117 and EP 0 352 944 describe a large family of N-phenyl-pyrazoles with a very broad spectrum of activity, including antiparasitic activity.

Although effective, N-phenylpyrazole derivatives, and in particular 5-amino-1-[2,6-dichloro-4-(trifluoro-methyl)phenyl]-4-(trifluoromethylsulfinyl)-1H-pyrazole-3-carbonitrile (fipronil), are occasionally difficult to formulate since they do not always have sufficient solubility in the excipients conventionally used for the preparation of ready-to-use liquid antiparasitic compositions.

Specifically, products that are active against blood-sucking parasites, and in particular against fleas, may especially be in the form of liquid compositions (pipettes) or solutions for applying to the skin, also known as "Spot-On solutions", to be applied very easily, in a single topical application directly to the animal's skin, generally between the shoulder blades.

However, in this type of composition, fipronil is often difficult to formulate and may lead to crystallization. In order to overcome this problem, it has already been proposed, especially in patent application EP 0 881 881, to formulate N-phenylpyrazole derivatives in solvent medium in the presence of a crystallization inhibitor and a $C_1$-$C_4$ alcohol. The product Frontline® Spot-On Chat et Chien, sold in France by the company Merial SAS, is based on this technology.

Although such compositions are suitable for preventing the crystallization problems of these particular active principles, they are, however, not entirely satisfactory as regards the duration of protection they give the animal. In the case of the product Frontline® Spot-On Chat et Chien especially, the duration of protection against new flea infestations stated by the manufacturer is limited to 4 weeks in the case of cats and to 2 months in the case of dogs. However, antiparasitic efficacy tests conducted according to the current standards do not make it possible to reproduce the prolonged efficacy results, and the product does not therefore always have entirely satisfactory remanence.

SUMMARY OF THE INVENTION

It is thus in order to overcome all the problems encountered with the antiparasitic products currently available on the market and to provide a product that can effectively prevent and treat flea infestations on pets, both cats and dogs, that the Applicant has developed the product that is the subject of the invention. The Applicant particularly set itself the aim of providing a product for preventing and treating flea infestations on pets that is easy to formulate and easy to apply, while at the same time being fast-acting and more remanent than the products currently available on the market.

Another object of the invention is to provide such compositions that are easy to use irrespective of the animal species, the size of the animal or the nature of its coat.

Another object of the invention is to provide efficient compositions that do not necessitate wetting of the entire animal.

These objects are achieved by the antiparasitic pharmaceutical composition that forms the subject of the present invention.

DETAILED DESCRIPTION OF THE INVENTION

Unexpectedly, the antiparasitic pharmaceutical composition of the invention provides effective and prolonged activity in the treatment and protection of pets in the form of a ready-to-use solution that is easy to use.

Thus, one subject of the present invention is a liquid pharmaceutical composition, characterized in that it contains:
- as active principle, 5-amino-1-[2,6-dichloro-4-(trifluoromethyl)phenyl]-4-(trifluoromethylsulfinyl)-1H-pyrazole-3-carbonitrile (fipronil),
- at least 5% (weight/volume) of benzyl alcohol, and
- at least 50% (weight/volume) of an organic solvent chosen from propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof,
- it being understood that said composition is free of $C_1$-$C_4$ alcohol.

According to the invention, said pharmaceutical composition is intended in particular to be applied to cats or to dogs.

In the pharmaceutical composition in accordance with the invention, fipronil preferably represents from 1% to 20% (weight/volume) and even more preferentially from 5% to 15% (weight/volume). It should be understood, however, that these amounts are given as a guide and that they may be adjusted according to the formulation requirements, in particular with regard to the effective doses as a function of the animal to be treated and its weight.

According to one preferred embodiment of the invention, benzyl alcohol represents from 5% to 40% (weight/volume) and even more preferentially from 25% to 35% (weight/volume).

The organic solvent(s) mentioned above are used in the amounts necessary to adjust the pharmaceutical composition to the required final volume. The weight/volume percentage of the organic solvent or of the mixture of organic solvents depends on the nature (and thus on the density) of the solvent or solvent mixture used.

Among said organic solvents, diethylene glycol monoethyl ether (DGME) is most particularly preferred.

The pharmaceutical composition used in accordance with the invention may also contain one or more excipients that may be chosen, for example, from surfactants, thickeners, dyes, fragrances and antioxidants, among which examples that may be mentioned, in a non-limiting manner, include butylhydroxyanisole, butylhydroxy-toluene, propyl gallate, ascorbyl palmitate and rosemary extracts, and mixtures thereof.

When it is (they are) present, the antioxidant(s) preferably represent from 0.005% to 2% approximately (weight/volume) and even more preferentially from 0.01% to 0.1% approximately (weight/volume).

Besides fipronil, the pharmaceutical composition may also contain one or more additional antiparasitic active principles. Additional antiparasitic active principles that may especially be mentioned include acaricides such as amitraz or cymiazole, flea and tick growth inhibitors, also known as "IGR" for "Insect Growth Regulators", such as pyriproxyfen and ethoxazole, endoparasiticides such as avermectins and derivatives thereof, for instance ivermectin, abamectin, doramectin and moxydectin, milbemycins, and also compounds that are active against pet ectoparasites and sand flies.

Such combinations of active agents may be useful for broadening the spectrum of action of the composition in accordance with the present invention.

The pharmaceutical composition in accordance with the invention may be readily prepared by simple dilution of fipronil and optionally of the additional antiparasitic active principle(s) in benzyl alcohol and the organic solvent(s) used.

After its preparation, the pharmaceutical composition is preferably conditioned in single-dose pipettes.

Another subject of the present patent application is the use of a liquid pharmaceutical composition as described previously for the preparation of an antiparasitic veterinary medicament for topical application for preventing (protecting) and/or treating flea infestations on pets, in particular on cats or dogs.

According to this use, said medicament is intended to be applied by direct application to the animal's skin, on the shoulder blades or along a dorsal line starting from the base of the tail and going up to the neck.

The amount of medicament to be administered may range from 0.3 to 1.5 ml approximately, preferably from 0.5 ml approximately for cats and from 0.3 to 6.0 ml approximately for dogs, as a function of the weight of the animal under consideration and the dosage.

The volume to be applied according to the invention should preferably correspond to a unit dose of fipronil ranging from 0.3 to 60 mg per kg of body weight and even more preferentially from 5 to 15 mg per kg of body weight.

Thus, according to one preferred embodiment of the invention, said medicament is intended to administer a unit dose of fipronil ranging from 0.3 to 60 mg per kg of body weight and even more preferentially from 5 to 15 mg per kg of body weight.

Besides the preceding provisions, the invention also comprises other provisions that will emerge from the description that follows, which refers to an example of preparation of a pharmaceutical composition in accordance with the invention, and also to examples demonstrating the efficacy of said composition in the treatment of fleas on cats and dogs.

It should be clearly understood, however, that these examples are given purely as illustrations of the subject of the invention, of which they do not in any way constitute a limitation.

Example 1

Antiflea Composition

The following antiflea composition was prepared, by simple dissolution of fipronil in the mixture of the other constituents of the composition:

| | |
|---|---|
| fipronil | 10.0 g |
| benzyl alcohol | 30.0 g |
| butylhydroxyanisole | 0.02 g |
| butylhydroxytoluene | 0.01 g |
| diethylene glycol monoethyl ether | qs 100 ml |

After preparation, this composition may be conditioned directly in single-dose pipettes.

Example 2

Study of the Immediate and Prolonged Efficacy of a Composition in Accordance with the Invention Against Fleas on Dogs In this example, a study was performed to determine and compare the immediate and prolonged efficacy of two fipronil-based topical compositions:
- a composition A in accordance with the invention as described above in Example 1;
- the product sold under the name Frontline® Spot-on dog by the company Mérial.

1) Materials and Methods
a) Type of Study
This is a randomized blind controlled efficacy study, performed in parallel on 3 groups of eight dogs.
b) Animals Used and Maintenance Conditions
The dogs used in this study were male or female adult domestic dogs, more than 4 months old, of mixed breeds, but mainly of short-hair European breed, weighing between 2 and 20 kg. Before the start of the study, all the dogs were checked to ensure that they were in good health, that they were not infested with fleas and that the females were not pregnant. All the dogs were wormed and acclimatized to the living conditions for at least 7 days before the start of the study.

During the acclimatization period and throughout the study period, the dogs were kept in an air-conditioned room, each dog being confined in an individual enclosure of dimensions 1.9 m×2.97 m without litter and without possible contact between the various dogs engaged in the study. The identification number, the group number and the type of composition administered were noted on the outside of each enclosure. The temperature of the room was maintained at about 20° C.±4° C. The dogs were subjected to an alternation of 12 hours of light and 12 hours of darkness.

The animals were fed once a day with commercial dog kibbles sold under the trade name Eukanuba® by the company Iams, a division of Foodcorp., according to the manufacturer's recommendations, and they were given free access to fresh drinking water.

c) Compositions Tested
Composition A in accordance with the invention was compared with the product Frontline® Spot-on dog containing 10% (g/100 ml) of fipronil and a mixture of excipients. It was used as supplied by the manufacturer.
d) Treatments
Group 1: Treatment with composition A in a proportion of 0.67 ml per dog for dogs weighing between 2 and 10 kg, and in a proportion of 1.34 ml per dog for dogs weighing between more than 10 kg and 20 kg,
Group 2: Treatment with the product Frontline® Spot-on dog in a proportion of 0.67 ml per dog for dogs weighing between 2 and 10 kg, and in a proportion of 1.34 ml per dog for dogs weighing between more than 10 kg and 20 kg,
Group 3: Negative control: no treatment.
The treatment was applied topically, between the dogs' shoulder blades, in a single application at the start of the study (D=0).
e) Flea Infestations/Measurement of the Efficacy of the Treatments
6 days before the start of the study (D=−6), all the dogs were infested with about 100 laboratory fleas, of the strain *Ctenocephalis felis*, of male or female sex. The fleas were then counted 4 days before the start of the treatment (D=−4). To do this, all the fleas present on an animal are harvested by combing the dog and then counted after combing. The number of fleas is thus determined. After counting, the fleas are destroyed and a new batch of about 100 fleas is placed on the animal the day prior to administration of the treatment (D=−1).

The number of fleas still alive 2 days after the administration of the test composition (D=2) was then counted.

The dogs were again infested with a known amount of fleas (about 100) 7 days (D=7), 14 days (D=14), 21 days (D=21), 28 days (D=28), 35 days (D=35), 42 days (D=42), 49 days (D=49), 56 days (D=56), 63 days (D=63), 70 days (D=70), 77 days (D=77), 84 days (D=84) and 91 days (D=91) after administration of the treatment.

Counting of the fleas that were still alive was then performed 48 hours after each of these new infestations (D=9; D=16; D=23; D=30; D=37; D=44; D=51; D=58; D=65; D=72; D=79; D=86 and D=93).

On each counting, the efficacy of the treatment was calculated according to the following equation:

% efficacy=100×($NP_vC-NP_vT$)/$NP_vC$ in which:
$NP_vC$ is the geometric average of the number of live fleas counted on the dogs of group 3 (control);
$NP_vT$ is the geometric average of the number of live fleas counted on the dogs of a group that has received a treatment (group 1 or 2).
A treatment is said to be effective if the percentage efficacy is greater than or equal to 95%.
2) Results
The average results obtained are given in Table I below:

TABLE I

| Days | GROUP 1 (Composition A) | GROUP 2 (Frontline ® Spot-on dog) |
|---|---|---|
| D = 2 | 99.7 | 100.0 |
| D = 9 | 100.0 | 100.0 |
| D = 16 | 99.8 | 100.0 |
| D = 23 | 100.0 | 100.0 |
| D = 30 | 100.0 | 100.0 |
| D = 37 | 100.0 | 100.0 |
| D = 44 | 99.9 | 100.0 |

TABLE I-continued

| Days | GROUP 1 (Composition A) | GROUP 2 (Frontline ® Spot-on dog) |
|---|---|---|
| D = 51 | 100.0 | 100.0 |
| D = 58 | 100.0 | 99.6 |
| D = 65 | 99.9 | 99.3 |
| D = 72 | 99.8 | 98.2 |
| D = 79 | 98.9 | 96.4 |
| D = 86 | 99.2 | 85.5 |
| D = 93 | 97.1 | 75.4 |

These results show that:
composition A in accordance with the present invention remains effective (determination 48 hours after the infestation) for 13 weeks (D=93) against flea infestations on dogs;
the product Frontline® Spot-on dog remains effective (determination 48 hours after infestation) only for 11 weeks (D=79) against flea infestations on dogs.

The efficacy and the better remanence of the composition A in accordance with the present invention are thus clearly demonstrated.

Example 3

Study of the Efficacy of a Composition in Accordance with the Invention Against Fleas on Dogs In this example, a study was performed to determine and compare the efficacy of two fipronil-based topical compositions:
a composition A in accordance with the invention and as described above in Example 1;
the product sold under the name Frontline® Spot-on dog by the company Mérial.

1) Materials and Methods a) Type of Study

This is a randomized blind controlled efficacy study performed in parallel on 3 groups of six dogs.

b) Animals Used and Maintenance Conditions

The dogs used in this study were male or female mongrels belonging to the species *Canis familiaris*, more than 6 months old, weighing between 6 kg and 25 kg. Before the start of the study, all the dogs were checked to ensure that they were in good health and that they were not infested with fleas. All the dogs were wormed and acclimatized to the living conditions for at least 7 days before the start of the study.

The dogs were also checked to ensure that they had not received any topical flea treatment in the 12 weeks preceding the start of the study.

During the acclimatization period and throughout the study, the dogs were kept in an air-conditioned room, each dog being confined in an individual enclosure of dimensions 1.9 m×2.97 m without litter and with no possible contact between the various dogs engaged in the study. The identification number, the group number and the type of composition administered were noted on the outside of each enclosure. The temperature of the room was maintained at about 20° C.±4° C. The dogs were subjected to an alternation of 12 hours of light and 12 hours of darkness.

The animals were fed once a day with commercial dog kibbles sold under the trade name Ultradog Superwoof by the company Nola, a division of Foodcorp., according to the manufacturer's recommendations, and were given free access to fresh drinking water.

c) Compositions Tested

Composition A in accordance with the invention was compared with the product Frontline® Spot-on dog containing 10% (g/100 ml) of fipronil and a mixture of excipients. It was used as supplied by the manufacturer.

d) Treatments

Group 1: Treatment with composition A in a proportion of 0.067 ml per kg of body weight,
Group 2: Treatment with the product Frontline® Spot-on dog in a proportion of 0.067 ml per kg of body weight,
Group 3: Negative control: no treatment.

The treatment was applied topically, between the dogs' shoulder blades, in a single application at the start of the study (D=0).

e) Flea Infestations/Measurement of the Efficacy of the Treatments 6 days before the start of the study (D=−6), all the dogs were infested with about 100 laboratory fleas, of the strain *Ctenocephalis felis*, of male or female sex. The fleas were then counted 5 days before the start of the treatment (D=−5). To do this, all the fleas present on an animal are harvested by combing the dogs and then counted after combing. The number of fleas is thus determined. After counting, the fleas are destroyed and a new batch of about 100 fleas is placed on the animal the day prior to administration of the treatment (D=−2).

The number of fleas still alive 1 day after administration of the composition (D=1) was then counted.

The dogs were again infested with a known amount of fleas (about 100) 7 days (D=7), 14 days (D=14), 21 days (D=21), 35 days (D=35), 42 days (D=42), 49 days (D=49) and 56 days (D=56) after administration of the treatment.

The fleas that were still alive were then counted 24 hours after each of these new infestations (D=8; D=15; D=22; D=36; D=43; D=50 and D=57).

At each counting, the efficacy of the treatment was calculated according to the following equation:

$$\% \text{ efficacy} = 100 \times (NP_vC - NP_vT)/NP_vC$$

in which:
$NP_vC$ is the geometric average of the number of live fleas counted on the dogs of group 3 (control);
$NP_vT$ is the geometric average of the number of live fleas counted on the dogs of a group that has received a treatment (group 1 or 2).

A treatment is said to be effective if the percentage efficacy is greater than or equal to 95%.

2) Results

The average results obtained are given in Table II below:

TABLE II

| Days | GROUP 1 (Composition A) | GROUP 2 (Frontline ® Spot-on dog) |
|---|---|---|
| D = 1 | 92.2 | 84.4 |
| D = 8 | 99.5 | 99.8 |
| D = 15 | 100.0 | 99.8 |
| D = 22 | 99.6 | 100.0 |
| D = 29 | 100.0 | 98.7 |
| D = 36 | 100.0 | 96.9 |
| D = 43 | 99.2 | 96.8 |
| D = 50 | 97.0 | 93.7 |
| D = 57 | 89.4 | 74.8 |

These results show that:
composition A acts more quickly than the product Frontline® Spot-on dog (comparison of the % efficacy values at D=1);

composition A in accordance with the present invention remains effective (determination 24 hours after infestation) for 7 weeks (D=50) against flea infestations on dogs;

the product Frontline® Spot-on dog remains effective (determination 24 hours after the infestation) only for 6 weeks (D=43) against flea infestations on dogs.

The speed of action and the better remanence of composition A in accordance with the present invention are thus clearly demonstrated.

Example 4

Study of the Efficacy of a Composition in Accordance with the Invention Against Fleas on Cats In this example, a study was performed to determine and compare the efficacy of two fipronil-based topical compositions:
- a composition A in accordance with the invention and as described in Example 1;
- the product sold under the name Frontline® Spot-on cat by the company Mérial.

1) Materials and Methods
a) Type of study

This is a randomized, blind controlled efficacy study performed in parallel on 3 groups of six cats.

This study was performed according to the Good Laboratory Practices for the evaluation of veterinary products (ENV/MC/CHEM/(98)17; decree of Jan. 28, 2005, published in the Official Gazette of Feb. 20, 2005) and according to the guideline recommendations of the Committee for Veterinary Medicinal Products (CVMP): "*Guidelines for the testing and evaluation of the efficacy of antiparasitic substances for the treatment and prevention of tick and flea infestations in dogs and cats*", EMEA/CVMP/005/2000-Rev. 2).

b) Animals Used and Maintenance Conditions

The cats used in this study were male or female adult European domestic cats, from 7 months to 2 years old, weighing on average 6.7±0.1 kg. All the cats were acclimatized to the living conditions for at least 9 days before the start of the study.

During the acclimatization period and throughout the study period, the cats were kept in an air-conditioned room, each cat being confined in individual cages. The identification number, the group number and the type of composition administered were noted on each cage. The temperature of the room was maintained at about 23° C.±2° C. with a relative humidity of 60±10%.

The animals were fed once a day (except for Sundays) with commercial cat kibbles, sold by the company Harlan-Teklad under the manufacturer's recommendations, and they were given free access to fresh drinking water.

c) Compositions Tested

Composition A in accordance with the invention was compared with the product Frontline® Spot-on cat containing 10% (g/100 ml) of fipronil and a mixture of excipients. It was used as supplied by the manufacturer.

d) Treatments

Group 1: Treatment with composition A in a proportion of 0.5 ml per cat, i.e. 50 mg of fipronil per animal, Group 2: Treatment with the product Frontline® Spot-on cat in a proportion of 0.5 ml per cat, i.e. 50 mg of fipronil per animal, Group 3: Negative control: no treatment.

The treatment was applied topically, between the shoulder blades of the cats, in a single application at the start of the study (D=0).

e) Flea Infestations/Measurement of the Efficacy of the Treatments

Nine days before the start of the study (D=−9), all the cats were infested with about 50 laboratory fleas, of the strain *Ctenocephalis felis*, of male or female sex. The fleas were then counted before the start of the treatment so as to check the capacity of each of the cats to host fleas. To perform counting, all the fleas present on an animal are harvested by combing the cat, and are then counted after combing. The number of fleas is thus determined. After counting, the fleas are destroyed and a new batch of about 50 fleas is placed on the animal the day prior to administration of the treatment (D=−1).

The first infestation took place the day before the treatment (D=−1).

The reinfestations then took place on D=7, D=14, D=21, D=28, D=35, D=42 and D=49.

The fleas were counted 48 hours after administration of the treatment and then 48 hours after each of the reinfestations (D=9, D=16, D=23, D=30, D=37, D=44 and D=51).

To do this, all the fleas present on an animal are harvested by combing the cat, and are then counted after combing. The number of live fleas is thus determined. After each counting, 50 new live fleas are placed on the cat.

At each counting, the efficacy of the treatment was calculated according to the following equation:

$$\% \text{ efficacy} = 100 \times (NP_vC - NP_vT)/NP_vC$$

in which:
$NP_vC$ is the geometric average of the number of live fleas counted on the cats of group 3 (control);
$NP_vT$ is the geometric average of the number of live fleas counted on the cats of a group that has received a treatment (groups 1 or 2).

A treatment is said to be effective if the percentage efficacy is greater than or equal to 95%.

2) Results

The results obtained are represented in Table III below, which gives, for each group, the percentage of dead fleas (geometric averages) counted at various times after infestation:

TABLE III

| Days | GROUP 1 (Composition A) | GROUP 2 (Frontline ® Spot-on cat) |
|---|---|---|
| D = 2 | 95.1 | 99.4 |
| D = 9 | 100.0 | 100.0 |
| D = 16 | 99.2 | 100.0 |
| D = 23 | 100.0 | 100.0 |
| D = 30 | 99.7 | 100.0 |
| D = 37 | 99.7 | 96.0 |
| D = 44 | 96.3 | 74.3 |
| D = 51 | 95.6 | 64.1 |

Monitoring of the local tolerance was performed 1 hour, 6 hours, 24 hours and 48 hours after application of the treatment. During these observations, a few cosmetic changes at the site of application of composition A were noted, in particular including matting (hairs stuck together with formation of tufts) and a greasy appearance 1 hour and 6 hours after application. A few white deposits (white powder, crystals) at the end of the hairs were moreover observed at 24 hours and 48 hours after application of the treatment. However, no sign of local or general intolerance was reported for composition A throughout the test.

These results demonstrate that:

composition A in accordance with the present invention remains effective (determination 48 hours after the infestation) for 7 weeks (D=51) against flea infestations on cats;

the product Frontline® Spot-on cat remains effective (determination 48 hours after the infestation) only for 5 weeks (D=37) against flea infestations on cats.

The efficacy and better remanence of composition A in accordance with the present invention are thus clearly demonstrated.

The invention claimed is:

1. A liquid pharmaceutical composition, comprising:
 as active principle, 5-amino-1-[2,6-dichloro-4-(trifluoromethyl)phenyl]-4-(trifluoromethylsulfinyl)-1H-pyrazole-3-carbonitrile (fipronil),
 at least 5% (weight/volume) of benzyl alcohol, and at least 50% (weight/volume) of an organic solvent chosen from propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof,
 it being understood that said composition is free of $C_1$-$C_4$ alcohol.

2. The composition as claimed in claim 1, wherein the fipronil represents from 1% to 20% (weight/volume).

3. The composition as claimed in claim 2, wherein the fipronil represents from 5% to 15% (weight/volume).

4. The composition as claimed in claim 1, wherein the benzyl alcohol represents from 25% to 35% (weight/volume).

5. The composition as claimed in claim 1, wherein the organic solvent is diethylene glycol monoethyl ether.

6. The composition as claimed in claim 1, wherein the composition also contains one or more excipients chosen from surfactants, thickeners, dyes, fragrances and antioxidants.

7. The composition as claimed in claim 6, wherein the antioxidants are chosen from butylhydroxyanisole, butylhydroxytoluene, propyl gallate, ascorbyl palmitate and rosemary extracts, and mixtures thereof.

8. The composition as claimed in claim 6, wherein, when they are present, the antioxidant(s) represent from 0.005% to 2% (weight/volume).

9. The composition as claimed in claim 1, wherein the composition comprises one or more additional antiparasitic active principles.

10. The composition as claimed in claim 9, wherein the additional antiparasitic active principles are chosen from acaricides, flea and tick growth inhibitors, endoparasiticides and active principles against pet ectoparasites and sand flies.

11. A method for the prevention and/or treatment of pet flea infestations comprising topically applying a liquid pharmaceutical composition as described in claim 1 to an animal in need thereof.

12. The method of claim 11, wherein the animal is a cat or a dog.

13. The method of claim 11, wherein said pharmaceutical composition is administered in an amount ranging from 0.3 to 1.5 ml to cats.

14. The method of claim 11, wherein said pharmaceutical composition is administered in an amount ranging from 0.3 to 6 ml to dogs.

15. The method of claim 11, wherein said pharmaceutical composition is administered in a unit dose of fipronil ranging from 5 to 15 mg per kg of body weight.

\* \* \* \* \*